United States Patent [19]

Ebisawa et al.

[11] Patent Number: 5,298,648
[45] Date of Patent: Mar. 29, 1994

[54] METHOD OF CRYSTALLIZING ASPARTAME

[75] Inventors: Kazuyoshi Ebisawa; Rie Kawaoka; Nobuya Nagashima; Satoshi Kumon, all of Kawasaki, Japan

[73] Assignee: Ajinomoto Co., Inc., Tokyo, Japan

[21] Appl. No.: 876,427

[22] Filed: Apr. 30, 1992

[30] Foreign Application Priority Data

May 9, 1991 [JP] Japan .................................. 3-199736

[51] Int. Cl.⁵ .......................................... C07C 101/02
[52] U.S. Cl. ......................................... 560/41; 560/40
[58] Field of Search ...................... 560/41, 40; 562/450

[56] References Cited

U.S. PATENT DOCUMENTS

| | | | |
|---|---|---|---|
| 3,678,026 | 7/1972 | Ariyoshi et al. | 560/41 |
| 4,684,745 | 8/1987 | Takemoto | 560/41 |
| 4,760,164 | 7/1988 | Park | 560/41 |
| 4,831,180 | 5/1989 | Wakamatsu | 560/41 |
| 5,097,060 | 3/1992 | Naruse | 560/41 |

FOREIGN PATENT DOCUMENTS 0128694 12/1984 European Pat. Off. .
0311985 4/1989 European Pat. Off. .

Primary Examiner—José G. Dees
Assistant Examiner—Samuel Barts
Attorney, Agent, or Firm—Oblon, Spivak, McClelland, Maier & Neustadt

[57] ABSTRACT

Aspartame, crystallized in the presence of a crystal growth inhibitor comprising one or more of dipeptides, amino acids, saccharides, organic acids and inorganic salts, has a thick and firm crystal habit. The crystals may be easily separated by solid-liquid separation, and the drying load of them is low. After being dried, the dried aspartame powder may be handled with ease and it has excellent powdery characteristics.

10 Claims, No Drawings

METHOD OF CRYSTALLIZING ASPARTAME

BACKGROUND OF THE INVENTION

1. Field of the Invention

The present invention relates to a method of crystallizing aspartame or L-α-aspartyl-L-phenylalanine methyl ester and the crystalline aspartame afforded by such a method.

2. Discussion of the Background

Aspartame, which is well known is a low-calorie sweetener having a high sweetness, is produced by various methods.

In the industrial production of aspartame, crystallization of aspartame is indispensable in any method for isolating it from a reaction solution to finally obtain the aspartame product. For such crystallization, in general, a method has heretofore been employed in which (i) a crude product containing aspartame is re-dissolved in water, an organic solvent or a water-containing organic solvent; (ii) the resulting solution is cooled by heat-exchange with a coolant (forced circulation indirect cooling system) or by evaporating a part of the solvent under a reduced pressure (self-evaporation system), in a crystallizer equipped with a stirrer so as to precipitate crystals, and (iii) the thus-formed crystals are removed by filtration and dewatering with a centrifugal separator or the like.

However, the aspartame afforded by the method has a fine needle-like and extremely fine cotton whisker-like crystal habit so that the solid-liquid separatability of the aspartame crystals by filtration and dewatering is extremely poor. Because of these effects, the above-mentioned method is seriously flawed for practical purposes.

In addition, in the drying step following the crystallization step, the drying load of the cake of the crystals is naturally high in view of the water content therein, and the bulk specific volume of the dried powder obtained is large so that handling of the powder is extremely difficult.

Further, since such crystals are a fine powder after being dried, they easily scatter, or that is, powdering and scattering of the dried powder from the crystals is noticeable. Moreover, the dried powder with such a fine powdery form has a small dissolution rate as it contains much air in the voids between the fine particles of the powder. Because of these reasons, the powdery aspartame has still further problems with respect to its powdery characteristics.

Therefore, if aspartame crystals having a thick and firm crystal habit could be obtained, they would be extremely advantageous from the view of the process of producing them and the product themselves. As a means of overcoming the above-mentioned problems, a method (static crystallization method) of crystallizing aspartame from its aqueous solution by cooling the solution has already been proposed, in which an aqueous solution of aspartame is cooled by conductive heat transfer without imparting any forced flow, for example by mechanical stirring, thereto, whereby the aspartame is crystallized as bundle-like crystals where plural needle-like crystals are bundled up to seemingly form one crystals having a thick and firm crystal habit. For a discussion, Japanese Patent Publication No. 2-45638 is referred to.

Thus there remains a need for a method of crystallizing aspartame which is free of the above-described drawbacks. There also remains a need for the crystalline aspartame produced by such a method.

SUMMARY OF THE INVENTION

Accordingly, one object of the present invention is to overcome the problems in the prior art to provide a further improved, in particular static, crystallization method of crystallizing aspartame from its aqueous solution.

It is another object of the present invention to provide crystalline aspartame produced by such a process.

These and other objects, which will become apparent during the following detailed description, have been achieved by the inventors' discovery that when aspartame is crystallized from an aqueous solution in the presence of a crystal growth inhibitor, aspartame crystals having a thicker and firmer crystal habit can be obtained. On the basis of this finding, the present invention has been achieved.

Specifically, the present invention relates to a method of crystallizing aspartame from an aqueous solution, in which an aspartame crystal growth inhibitor is present in the aqueous solution, and to the crystalline aspartame produced by such a method.

DETAILED DESCRIPTION OF THE PREFERRED EMBODIMENTS

The aspartame crystal growth inhibitor referred to herein indicates a substance which may specifically inhibit the growth of aspartame crystals in the length direction of each crystal. Such crystal growth inhibitors include, as examples thereof, di-peptides such as L-glycyl-L-valine, L-glycyl-L-isoleucine, L-glycyl-L-serine, L-glycyl-L-tyrosine, L-glycyl-L-glutamine, L-alanyl-L-tryptophan, L-alanyl-L-threonine, L-alanyl-L-tyrosine, L-alanyl-L-glutamine, L-aspartyl-L-valine, L-aspartyl-L-leucine, L-aspartyl-L-tyrosine, L-aspartyl-L-tyrosine methyl ester, and L-aspartyl-L-glutamine; amino acids such as L-cysteine, L-glutamic acid, L-isoleucine, L-aspartic acid, L-asparagine, L-glutamine, L-lysine, L-tyrosine, and L-tryptophan; saccharides such as saccharose, amylose, and amylopectin; organic acids such as citric acid; and inorganic salts such as potassium chloride. Of the dipeptides, aspartyl dipeptides are generally preferred as having a large inhibiting activity. Among them, L-aspartyl-L-tyrosine and its methyl ester as well as L-aspartyl-L-glutamine are especially preferred, as having a noticeable inhibiting activity. Of the amino acids, L-cysteine and L-glutamic acid have a noticeable inhibiting activity. Of the saccharides, amylose and amylopectin have a noticeable inhibiting activity.

Incorporation of the crystal growth inhibitor into an aqueous aspartame solution may be effected by dissolving the inhibitor into the aqueous solution, for which either the inhibitor agent itself or a raw material containing the inhibitor agent may be added to the solution. The amount of the inhibitor agent which should be in the aqueous solution is such that thicker and firmer aspartame crystals than those obtained by a conventional crystallization method in the absence of the inhibitor agent may be obtained from the solution under the determined crystallization condition. The amount may be extremely easily-determined by anyone skilled in the art through some preexperiments. For instance, when L-aspartyl-L-tyrosine is used, the amount thereof is suitably from 0.1 to 5% by weight based on the weight of the aspartame as being dissolved in the solution, preferably 0.5 to 2% by weight.

As a crystallizing solvent, water may be used. The water as a crystallizing solvent may contain any other solvent such as methanol or ethanol, provided that the additional solvent does not interfere with the essential object of the present invention or it is not specifically a bar to the practice of the present invention.

In the present invention, the presence of an aspartame growth inhibitor in the aqueous solution of aspartame from which aspartame is crystallized is indispensable, and any other conventional crystallization conditions may apply to the present invention. For instance, for supersaturating aspartame in the aqueous solution thereof, any known means for cooling, condensation and addition of organic solvents may be employed. As a matter of course, the crystallization system may be kept static during the crystallization step. However, this is not indispensable, and the system may well be stirred, if desired.

Where the crystal growth inhibitor of the invention is used in a static crystallization method, thicker and firmer bundle-like aspartame crystals than those obtained in the absence of the inhibitor can be obtained. Where the inhibitor is used in a non-static crystallization method, thicker and firmer aspartame crystals than those obtained in the absence of the inhibitor can be obtained. As a result, the solid-liquid separatability of the crystals from the mother solution is improved and elevated so that the drying load onto the crystals is lowered and the powdery characteristics of the dried powder from the separated crystals are also improved.

Separation of the aspartame crystals as crystallized in accordance with the method of the present invention from the crystallization mother liquid as well as drying of the thus separated crystals may well be effected by any conventional methods, such as filtration, centrifugation, oven-drying, and air-drying.

The method of the present invention may apply not only to the purification of a crude product in the process of preparing aspartame but also to the improvement of the crystal habit of aspartame crystals having a poor crystal habit by recrystallizing them in accordance with the method of the present invention. Where a crude aspartame containing impurities of diketopiperazine (DKP), which is a cyclized product of aspartame, or L-α-aspartyl-l-phenylalanine is subjected to crystallization by the method of the present invention, the amount of the mother solution adhering to the solid after solid-liquid separation may be reduced, and the cake washing efficiency may be elevated, so that aspartame crystals free from such impurities can be obtained. For the same reasons, incorporation of the crystal growth inhibitor used into the product crystals finally obtained by crystallization may be prevented.

Other features of the invention will become apparent in the course of the following descriptions of exemplary embodiments which are given for illustration of the invention and are not intended to be limiting thereof.

EXAMPLES

Example 1

2 g of aspartame, 10 mg (0.5 wt. % to aspartame) of L-aspartyl-L-tyrosine and 100 ml of water were put in a 200 ml-beaker and dissolved under heat at 65 C. The resulting solution was allowed to stand as it was at room temperature (24° C.) without stirring (for static crystallization), and the crystals precipitated out were removed by filtration and dried.

The crystals had a mean diameter of 35 μm.

For comparison, crystallization of aspartame from the aqueous solution was carried out in the same manner as described above, except that no L-aspartyl-L-tyrosine was added to the solution. The crystals obtained had a mean diameter of 12.5 μm.

Example 2

1 g of aspartame, 15 mg (1.5 wt. % to aspartame) of L-aspartyl-L-tyrosine and 50 ml of water were put in a 100 ml-beaker and dissolved under heat at 65° C. with stirring at about 200 rpm with a magnetic stirrer. Then, the resulting solution was allowed to stand as it was overnight at room temperature (24° C.) with continuous stirring.

Of the slurry aspartame crystals thus-obtained, 70% (by weight) of the larger ones had a mean diameter of 12.5 μm.

For comparison, crystallization of aspartame from the aqueous solution was carried out in the same manner as described above, except that no L-aspartyl-L-tyrosine was added to the solution. 70 % (by weight) of the larger ones of the aspartame crystals thus obtained had a mean diameter of 7 μm.

In accordance with the present invention, there is provided a method of crystallizing aspartame crystals having a thick and firm crystal habit. The aspartame crystals as crystallized by the method of the invention may well be separated by solid-liquid separation, and the drying load of them is low. After being dried, the dried aspartame powder may be handled with ease and it has excellent powdery characteristics.

obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method of crystallizing aspartame, comprising crystallizing aspartame from a supersaturated aqueous solution of (i) aspartame and (ii) a compound selected from the group consisting of L-glycyl-L-valine, L-glycyl-L-isoleucine, L-glycyl-L-serine, L-glycyl-L-tyrosine, L-glycyl-L-glutamine, L-alanyl-L-tryptophan, L-alanyl-L-threonine, L-alanyl-L-tyrosine, L-alanyl-L-glutamine, L-aspartyl-L-valine, L-aspartyl-L-leucine, L-aspartyl-L-tyrosine, L-aspartyl-L-tyrosine methyl ester, L-aspartyl-L-glutamine, L-cysteine, L-glutamic acid, L-isoleucine, L-aspartic acid, L-asparagine, L-glutamine, L-lysine, L-tyrosine, L-tryptophan, saccharose, amylose, amylopectin, citric acid, and potassium chloride.

2. The method of claim 1, wherein said solution is formed by heating an aqueous mixture of aspartame and said compound to a temperature of 65° C.

3. The method of claim 1, wherein said solution is maintained static during said crystallizing.

4. The method of claim 1, wherein said solution is stirred during said crystallizing.

5. The method of claim 1, wherein said crystallizing comprises adding an organic solvent.

6. The method of claim 1, wherein said crystallizing comprises cooling said solution.

7. The method of claim 1, wherein said crystallizing comprises condensing said solution.

8. The method of claim 1, wherein said compound (ii) is present in an amount of from 0.1 to 5% by weight based on the weight of said aspartame in said aqueous solution.

9. The method of claim 1, wherein said compound (ii) is selected from the group consisting of L-aspartyl-L-valine, L-aspartyl-L-leucine, L-aspartyl-L-tyrosine, L-aspartyl-L-tyrosine methyl ester, and L-aspartyl-L-glutamine.

10. The method of claim 1, wherein said compound (ii) is selected from the group consisting of L-aspartyl-L-tyrosine, L-aspartyl-L-tyrosine methyl ester, and L-aspartyl-L-glutamine.

* * * * *